United States Patent [19]

Carpenter et al.

[11] Patent Number: 5,735,872
[45] Date of Patent: Apr. 7, 1998

[54] STENT

[75] Inventors: Kenneth W. Carpenter, Del Mar; Leo R. Roucher, Jr., Escondido; Eugene J. Jung, Jr., San Diego; Erich H. Wolf, Vista; Thomas A. Steinke, San Diego, all of Calif.

[73] Assignee: Navius Corporation, San Diego, Calif.

[21] Appl. No.: 720,714

[22] Filed: Oct. 2, 1996

Related U.S. Application Data

[63] Continuation-in-part of Ser. No. 557,725, Nov. 13, 1995, Pat. No. 5,643,314.

[51] Int. Cl.$^6$ .................................................. A61M 29/00
[52] U.S. Cl. .................................. 606/198; 623/1; 623/12
[58] Field of Search ................................ 606/191, 194, 606/195, 198, 200; 623/1, 12; 128/898, 899

[56] References Cited

U.S. PATENT DOCUMENTS

| | | |
|---|---|---|
| 3,278,176 | 10/1966 | Abolins . |
| 3,842,441 | 10/1974 | Kaiser . |
| 4,214,587 | 7/1980 | Sakura, Jr. . |
| 4,434,797 | 3/1984 | Silander . |
| 4,512,338 | 4/1985 | Balko et al. . |
| 4,553,545 | 11/1985 | Maass et al. . |
| 4,732,152 | 3/1988 | Wallsten et al. . |
| 4,733,665 | 3/1988 | Palmaz . |
| 4,739,762 | 4/1988 | Palmaz . |
| 4,740,207 | 4/1988 | Kreamer . |
| 4,776,337 | 10/1988 | Palmaz . |
| 4,793,348 | 12/1988 | Palmaz . |
| 4,800,882 | 1/1989 | Gianturco . |
| 4,856,516 | 8/1989 | Hillstead . |
| 4,878,906 | 11/1989 | Lindemann et al. . |
| 4,886,062 | 12/1989 | Wiktor . |
| 4,907,336 | 3/1990 | Gianturco . |
| 4,913,141 | 4/1990 | Hillstead . |
| 4,969,458 | 11/1990 | Wiktor . |
| 5,019,090 | 5/1991 | Pinchuk . |
| 5,344,426 | 9/1994 | Lau et al. . |
| 5,383,892 | 1/1995 | Cardon et al. . |
| 5,403,341 | 4/1995 | Solar . |
| 5,441,515 | 8/1995 | Khosravi et al. ............... 623/1 |
| 5,449,373 | 9/1995 | Pinchasik et al. . |
| 5,549,662 | 8/1996 | Fordenbacher ............... 606/198 |
| 5,556,413 | 9/1996 | Lam ............................. 606/198 |

*Primary Examiner*—William Lewis
*Attorney, Agent, or Firm*—Nydegger & Associates

[57] ABSTRACT

The present invention is a stent for insertion into an artery or other vessel. The stent is formed from a series of tubular shaped bands each formed with a first end which overlaps a second end. The overlap between the first and second ends is variable and allows each band to move between a contracted configuration and a fully expanded configuration which are within the elastic limits of the band. Each band includes a plurality of receivers and a first tab on a first edge of the band to secure each band at or near the fully expanded configuration and allow the stent to conform to the contours of the vessel. The bands are distributed along a substantially common axis to form a tube interconnected by a pair of elongated strips. In use, the stent is placed over a balloon catheter and compressed to adopt the contracted configuration. The stent is maintained in the contracted configuration by a retainer. The balloon catheter and stent are then advanced through a placement catheter to a target site where the balloon is partially inflated to free the stent for expansion to an equilibrium configuration. The balloon may then be more fully inflated to further expand any of the bands in the stent to suit the needs of the patient. The balloon is then deflated and removed, leaving the expanded stent to support that target site.

23 Claims, 3 Drawing Sheets

STENT

This application is a continuation-in part of applicants' application Ser. No. 08/557,725, filed Nov. 13, 1995, now U.S. Pat. No. 5,643,314 entitled "Self-Expanding Stent," the contents of which are incorporated herein by reference.

FIELD OF THE INVENTION

The present invention pertains generally to devices which are used for treatment of weakened or clogged arteries and other internal vessels. More specifically, the present invention pertains to devices which can be expanded within an artery or other vessel to prevent occlusion of the vessel. The present invention is particularly, but not exclusively, useful as a flexible, secure stent for insertion into an artery or vessel to support the vessel wall.

BACKGROUND OF THE INVENTION

The use of stents within vessels, such as arterial vessels, is well known. Generally, devices of this type are inserted into a vessel to support the vessel wall, and thus prevent the wall from collapsing and occluding the vessel. Alternatively, in a procedure commonly referred to as vascular repaving, stents may be inserted into a weakened portion of a vessel to prevent internal pressure within the vessel from causing the vessel wall to rupture. Accordingly, stents may be useful whenever a vessel wall has become weakened (such as by disease) or when the vessel becomes clogged (such as by the buildup of plaque), or whenever surrounding tissue (such as a tumor) is applying pressure to the outside of a vessel which may cause the vessel to collapse.

The benefits associated with the use of stents has resulted, not surprisingly, in the increased use of stents to treat an ever increasing number of maladies. As a result, a wide variety of differing stent designs have been developed, each of which may be more, or less, appropriate for the treatment of a particular condition. A contributing factor to the proliferation of differing stent types has been the problematic conditions faced as part of the design and fabrication of a beneficial stent. For example, it is readily appreciated that the operational environment into which a stent is to be placed may vary widely from the idealized conditions of a laboratory. Specifically, the vessel into which the stent is to be placed may be curved or otherwise tortuous. In such cases, insertion of an inflexible stent may be undesirable or even impossible. This particular difficulty is often avoided by the use of a shorter stent, or even a series of shorter stents. In either case, however, the treatment may be complicated or the efficacy of the treatment may be reduced.

Tapered vessels present another aspect of stent design which can be of concern. Tapered vessels, are of course, not uncommon and may even occur in combination with the curved vessel discussed in the preceding section. In cases with tapered vessels, the use of a stent which cannot conform to the changing diameter of the vessel may be problematic. Once again, the use of a series of shorter stents is possible, but this necessarily complicates the course of treatment.

The particular treatment site may also subject the stent to a relatively large compressive load. In such cases the use of a stent which recoils under the load would be inappropriate. The solution for many cases of this type is the utilization of a stronger, or more robust, stent. The use of a stronger stent may not be possible, however, if the stent is required to provide a high degree of flexibility such as when placement within a curved or tapered vessel is required.

Practice has also shown that the use and placement of stents in small vessels is particularly difficult. More specifically, at present, most stents are designed to be delivered in an unexpanded state and then expanded, in-situ, to support the vessel at the target site. In small vessels (generally those with a diameter of less than three millimeters), there may not be adequate room to allow passage of the stent. This may be so even with the stent in its unexpanded state. The use of smaller stents is possible, but may in itself be difficult if the stent is not strong enough to support the intended compressive load.

In light of the above, it is an object of the present invention to provide a vascular stent which can be inserted into a vessel to support the vessel wall. Another object of the present invention is to provide a vascular stent which can withstand a relatively large compressive load without recoiling. Another object of the present invention is to provide a vascular stent which can be inserted into relatively small vessels. Still another object of the present invention is to provide a vascular stent which expands substantially iso-concentrically to more nearly replicate the original lumen of a vessel and can be utilized in a curved or tapered vascular segment. Yet another object of the present invention is to provide a stent which reliably stays in position in the vessel. Still another object of the present invention is to provide a vascular stent which is relatively easy to manufacture, simple to operate and comparatively cost effective.

SUMMARY

The present invention provides a stent for placement into an artery or other vessel within a patient. Structurally, the present invention includes a series of interconnected tubular shaped bands. As detailed below, the interconnected bands expand to closely replicate the original lumen of the vessel, bend to fit a curved or tapered vascular segment and reliably stay in position in the vessel.

Each band is formed to have a first edge, a second edge, an inner surface and an outer surface. Each band is also non-continuous and includes a first end which overlaps a second end so that a portion of the inner surface of each band overlays and contiguously contacts a portion of the outer surface of the same band. For each band, the first end is movable relative to the second end to reconfigure the band between a tubular shaped, contracted configuration and a tubular shaped, fully expanded position.

Basically, the first end of each band moves along a path over the outer surface of the band, which is substantially concentric with a path of the second end of the band as it moves along the inner surface of the band. The movements of the first end and second end of the band along their respective paths create an overlap region which is able to increase or decrease. Functionally, this allows each band to move substantially iso-concentrically between the contracted configuration having a first diameter and the fully expanded configuration having a second diameter.

As provided herein, each band can be made of a resilient material and can be formed so that, absent some restraint, each band expands from the contracted position and approaches the fully expanded position. The amount that each band expands, absent restraint, can be controlled during the manufacture of the stent to suit the particular use of the stent.

For example, the plurality of interconnected bands can be manufactured from a thin sheet of resilient material such as stainless steel. The pattern of the bands in the stent can be chemically milled into the thin sheet. Next, the stent is rolled on a mandrel into a tubular shape with the first end of each band overlapping its second end. Preferably, the stent is rolled so that movement of each band between the contracted configuration and the fully expanded configuration is within the elastic limits of each band and an equilibrium configuration for each band is between the contracted configuration and the fully expanded configuration.

The term "equilibrium configuration" as used herein means the configuration each band is manufactured to assume in the absence of an external force to the band.

The term "elastic limit" as used herein means the point beyond which plastic deformation is present after the release of a load to the band. For example, if the band is contracted past its elastic limit, the band will not expand to the equilibrium configuration without providing an external force. Similarly, if the band is expanded past its elastic limit, the band will not contract to the equilibrium configuration without providing an external force. As long as the band is deflected within its elastic limits, the band will return to its equilibrium configuration in the absence of an external force.

At least one of the bands and more preferably all of the bands include a first tab and at least one receiver disposed on the first edge to retain the stent in the vessel. Structurally, the first tab is positioned proximate one of the ends, while the receiver is positioned proximate the other end. The first tab includes a receiver section that is on a plane which is substantially perpendicular to a central axis of the band. The receiver section securely engages the receiver and inhibits the tubular band from retracting toward the contracted configuration.

Preferably, the first tab is positioned proximate to the second end so that the receiver section is directed radially outward and does not interfere with the operation of a balloon used to install the stent. Further, the first tab can be folded above the outer surface to hold the first end of the band against the outer surface.

At least one band can include a plurality of receivers positioned at predetermined positions so that each band may be retained at a plurality intermediate expanded configurations between the contracted and fully expanded configurations. In one embodiment of the present invention, each of the retainers is a notch in the first edge having a depth which is substantially equal to "X," that is shaped to receive the receiver section of the first tab. Importantly, each notch is shaped to allow the receiver section to move past the notch as the band expands but inhibit the receiver section from moving past the notch when the band is subject to compression.

In the embodiment with a plurality of notches, the receiver section sequentially engages the notches as the band expands and inhibits the band from returning towards the contracted configuration when the band is subject to compression. Typically, the notches are positioned to engage the first tab only as the band nears and reaches the fully expanded configuration.

Optimally, each band includes a second tab and a protruding lip. The second tab projects from the second edge, proximate second end and substantially opposite the first tab. The second tab can be folded radially outward and over the outer surface of the band to hold the second end to the outer surface. The protruding lip extends outwardly from the second edge proximate the first end a distance which is approximately equal to "X." The protruding lip is located opposite the notches and cooperates with the second tab to draw the first tab into engagement with the notches.

Importantly, the first and second tabs allow the first and second ends of the band to move along their respective, substantially concentric paths. In this fashion, the ability of the band to move between the contracted configuration and the fully expanded configuration, by changing the overlap region between the first end and second end, is preserved.

Operationally, the stent while at its equilibrium configuration is first positioned to surround a portion of an inflatable balloon catheter. The stent, with the balloon catheter inside, is then compressed until each of the bands has substantially reached the contracted configuration. At this diameter, a retainer, e.g. an adhesive, may be used to selectively secure the first end of each band to its respective outer surface to hold the bands in the contracted configuration. This also locks the stent over the balloon catheter. A guide catheter is then inserted into the patient's body. The guide catheter is formed with a lumen and the stent and balloon are inserted into the lumen and advanced into the patient's body.

Inside of the patient's body, the stent and balloon catheter are advanced distally out of the placement catheter. The stent and balloon catheter are then advanced until the target site has been reached. With the stent positioned at the target site, the balloon is first partially inflated. This initial partial inflation of the balloon applies an expansive force to the inner surface of each of the bands that overcomes the retainer retaining the bands.

When freed, the bands, if made of a resilient material, undergo an initial expansion from the contracted configuration to its equilibrium configuration. Once the initial expansion is complete, the balloon can be further inflated to further expand each of the bands, if necessary. In particular, each of the bands is expanded until the first tab of each band has engaged with one of the notches that are formed in that particular band. Depending on which notch is engaged, the stent will assume either one of the intermediate expanded configurations or the fully expanded configuration. Further, the stent is securely maintained in position since the receiver section of each band securely engages one of the notches as a result of the unique cooperation and design of the first tab, the second tab, the notches and the protruding lip.

Subsequently, the balloon may be deflated and removed or reinflated to further expand specific, partially expanded bands within the stent. As can be easily appreciated, the differential expansion of the bands allows the stent to adapt to tapered or otherwise irregular vessels. In all cases, with the expanded stent positioned to support the vessel wall at the target site, the balloon is deflated and the balloon and placement catheter are withdrawn from the vessel to complete the procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
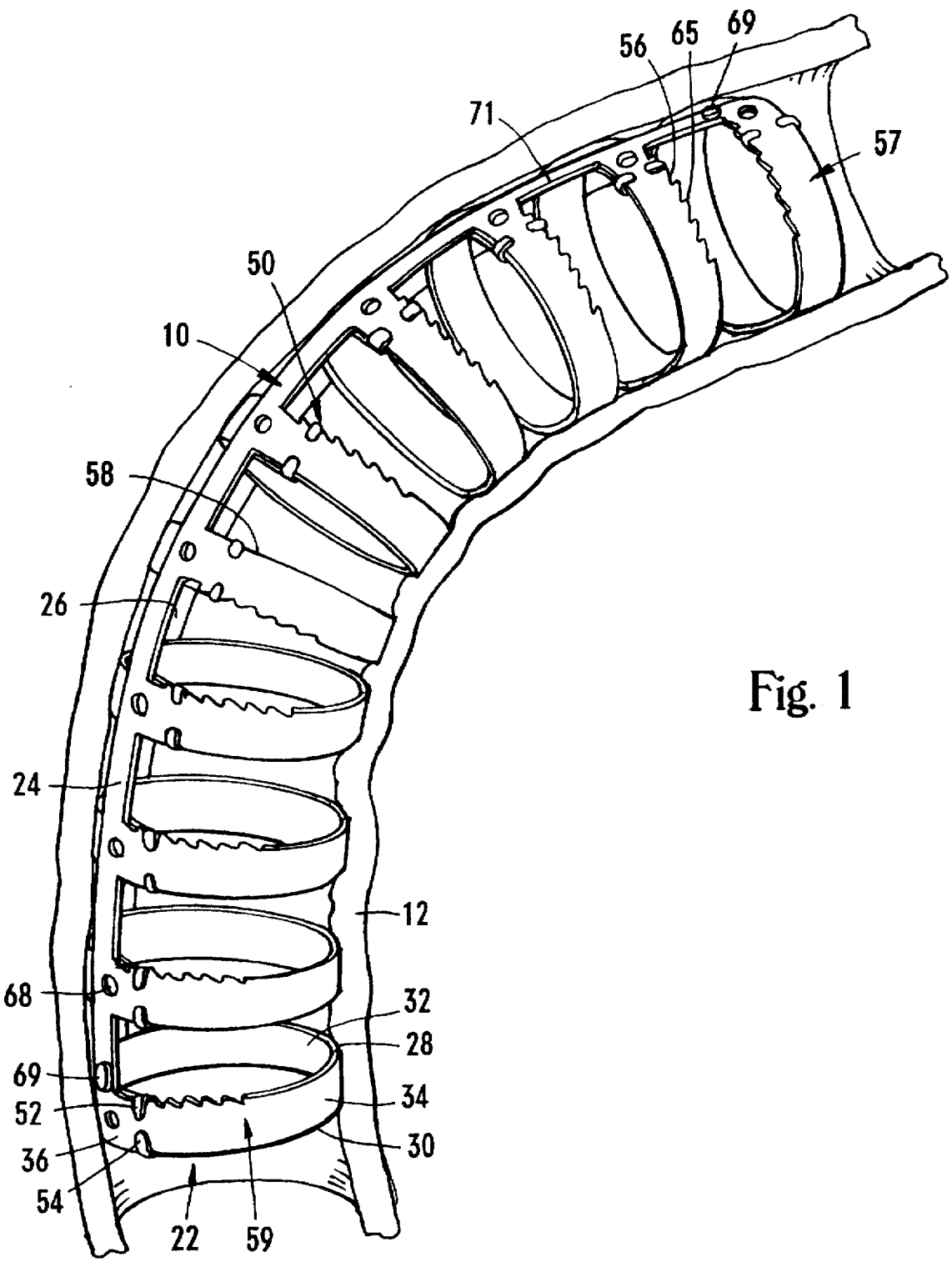
FIG. 1 is a representation of a stent having features of the present invention, positioned within a vessel of a patient.

Referring initially to FIG. 1, a stent 10 for structurally supporting the wall of a vessel 12 in accordance with the present invention is disclosed herein. For purposes of illustration, the stent 10 is shown operationally positioned in a vessel 12 in a patient. It should be appreciated, that the stent 10 is useful in vessels 12 throughout the vascular system of the patient and may be introduced into the vessel 12 wherever it is most convenient to do so.

Figure 2:
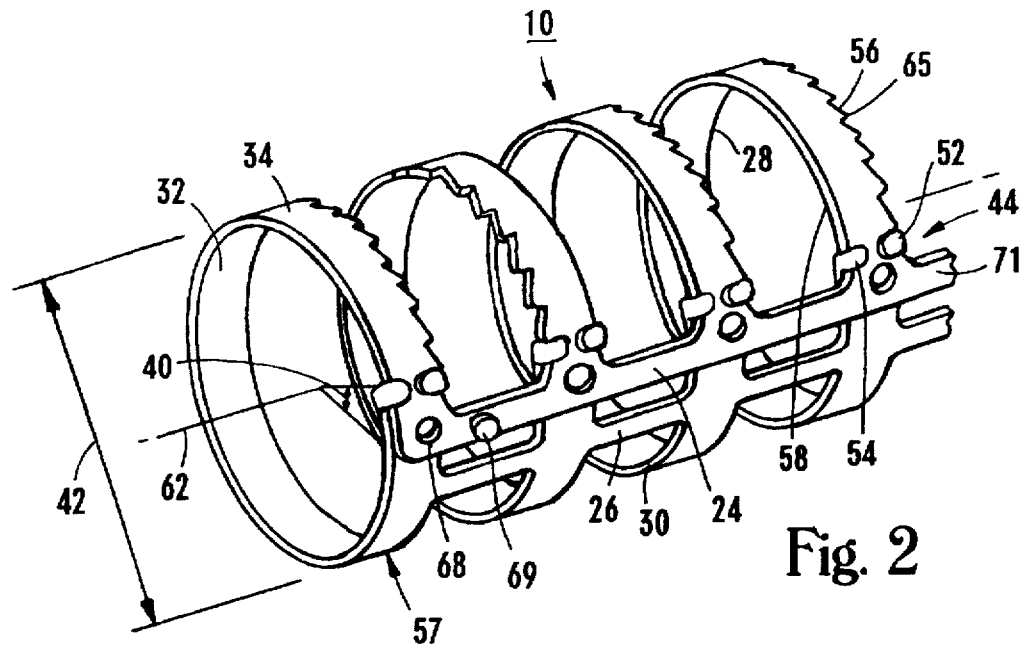
FIG. 2 is an isometric view of the stent FIG. 1 shown in a fully expanded configuration.
Figure 3:
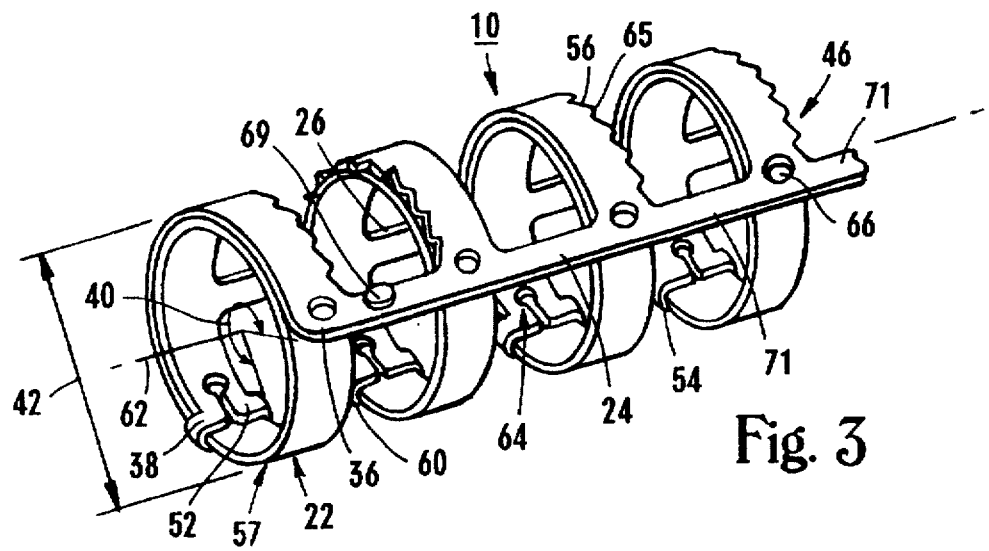
FIG. 3 is an isometric view of the stent of FIG. 1 in an equilibrium configuration.
Figure 4:
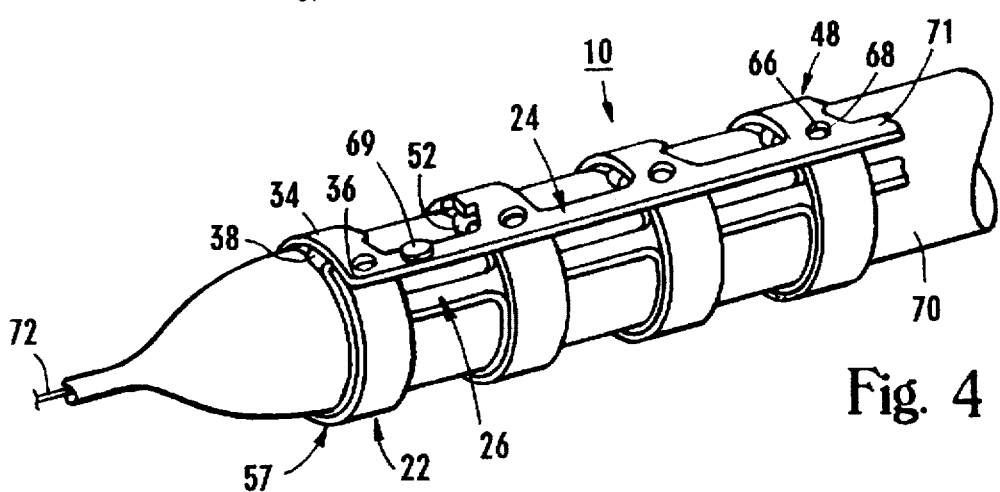
FIG. 4 is an isometric view of the stent of FIG. 1 shown in a contracted position on a balloon that is deflated.
Figure 5:
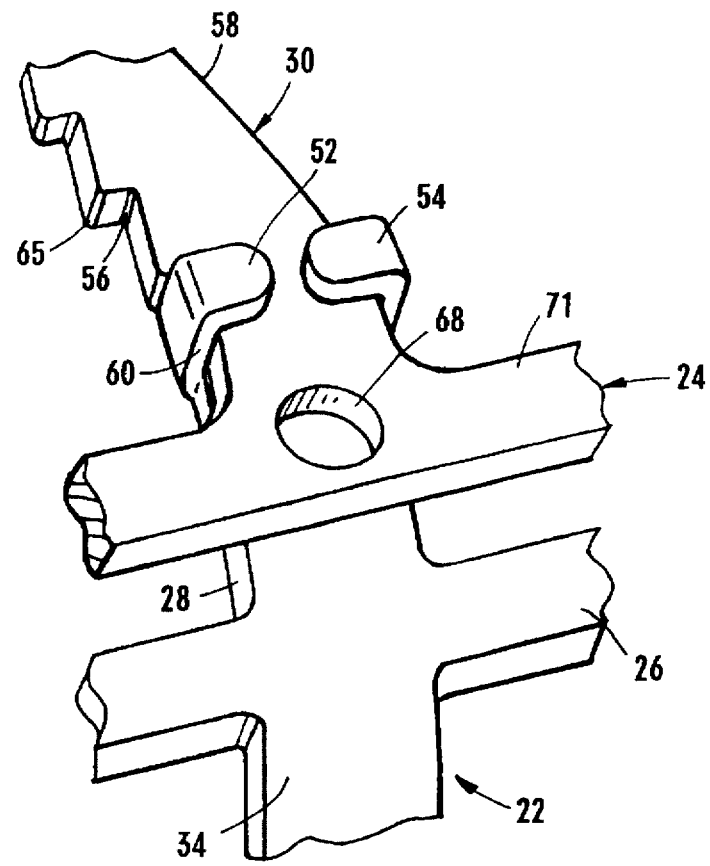
FIG. 5 is an expanded, isometric view of a portion of the stent of FIG. 2.

Referring now to FIGS. 2–4, it may be seen that the stent 10 is an elongated tube formed from a series of tubular shaped bands 22. The bands 22 are interconnected by a first elongated strip 24 and a second elongated strip 26. Each band 22 is formed to have a substantially circular shape, a first edge 28, a second edge 30, an inner surface 32 and an outer surface 34. Each band 22 is formed to be non-continuous. As a result, each band 22 has a first end 36 and a second end 38.

The first end 36 and second end 38 partially overlap each other so that a portion of the inner surface 32 of each band 22 overlays and contiguously contacts a portion of the outer surface 34 of the same band 22. Importantly, for each band 22, the first end 36 is moveable over the outer surface 34 and the second end 38 is moveable over the inner surface 32.

The movement of the first end 36 and second end 38 provides an overlap region 40 between the first end 36 and the second end 38 of each band 22. Increasing or decreasing the overlap region 40 of the band 22 causes a corresponding increase or decrease in the diameter 42 of the band 22.

For each band 22, the relationship between the overlap region 40 and the diameter 42 may be more easily appreciated by comparison between FIG. 2, where the bands 22 are shown in a fully expanded configuration 44, FIG. 3, where the bands 22 are shown in an equilibrium configuration 46, and FIG. 4, where the bands 22 are shown in a contracted configuration 48. Specifically, it may be seen that the overlap region 40 of FIG. 2 increases in FIG. 3 and further increases in FIG. 4. It may also be seen that the diameter 42 in FIG. 2, decreases in FIG. 3 and further decreases in FIG. 4. Thus, movement of the first end 36 relative to the second end 38 varies the overlap region 40 and allows the bands 22 to move between the fully expanded configuration 44 shown in FIG. 2 and the contracted configuration 48 shown in FIG. 4.

Returning to FIGS. 2–4, at least one of the bands 22 can include a first tab 52, a second tab 54, a plurality of receivers 56 and a protruding lip 58 to secure the band 22 at the fully expanded configuration 44 or one of the intermediate expanded configurations 50 between the contracted configuration 48 and the fully expanded configuration 44. For the purposes of the present invention, any number of the bands 22 can include these components. Preferably, referring to FIG. 1, each band 22 includes these components so that the stent 10 is securely retained in the vessel 12 and each band 22 of the stent 10 can be expanded to conform to the contours of the vessel 12.

In the embodiment shown in the Figures, the first tab 52 and second tab 54 are positioned proximate the second end 38. The first tab 52 projects from the first edge 28 while the second tab 54 projects from the second edge 30. The first tab 52 includes a receiver section 60 for interacting with the receivers 56 and retaining the band 22 expanded from the contracted position 48 in one of the intermediate expanded configurations or the fully expanded configuration 44. The receiver section 60 is disposed in a plane which is substantially perpendicular to a central axis 62 of the bands prior to installation into the vessel 12. This design of the receiver section 60 ensures good contact between the receiver section 60 and each receiver 56.

In the embodiment shown in the Figures, both the first tab 52 and the second tab 54 are folded radially outward and over the outer surface 34 and the receiver section 60 of the first tab 52 is defined by the radial outward portion of the first tab 52.

Functionally, first tab 52 and second tab 54 function as a clasp which hold the first end 36 against the outer surface 34. Importantly, the first tab 52 and the second tab 54 allow each band 22 to move between the contracted configuration 48 of FIG. 4 and the fully expanded configuration 44 of FIG. 2.

Preferably, at least a portion of the first tab 52 and the second tab 54 are annealed to allow the tabs 52, 54 to be folded radially outward and over the outer surface 34. Further, the annealing of the tabs 52, 54 may provide flexibility as the first tab 52 moves over the receivers 56 and as the stent 10 flexes in the vessel 12.

Figure 6:
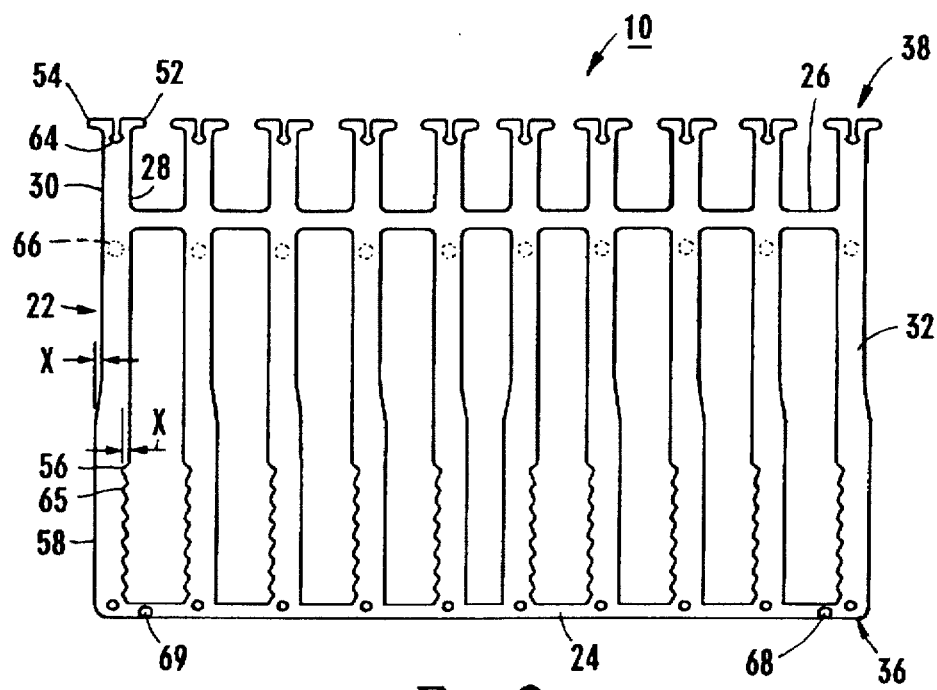
FIG. 6 is a front plan view of a thin sheet prior to being shaped into a stent having features of the present invention.

Referring to FIG. 6, a relief 64, e.g., a slot, can be disposed between the first tab 52 and the second tab 54 to provide additional flexibility to the tabs 52, 54 during expansion of the bands 22 and during use in the vessel 12. Basically, the relief 64 allows the tabs 52, 54 to separate as the first tab 52 moves over each receiver 56 and causes the tabs 52, 54 to pull together therebetween.

The structural details of the band 22 may be more fully appreciated by reference to FIG. 6 where a plurality of bands 22 are shown in an unrolled configuration and the first tab 52 and the second tab 54 have not been folded radially outward and over the outer surface 34. Further, the receivers 56 and protruding lip 58 are also clearly visible from FIG. 6.

The receivers 56 receive and retain the first tab 52. The receivers 56 can be implemented in a number of ways. For example, in the embodiment shown in the Figures, each receiver 56 is a notch formed into the first edge 28 of the band 22 having a depth which is substantially equal to "X." In the embodiment shown in the Figures, the notches are shaped to receive the receiver section 60 of the first tab 52 and have a depth of between about 0.002 to 0.010 inches. Referring to FIG. 6, each notch is substantially right triangular shaped and designed to facilitate movement of the first tab 52 in one direction over the notch and inhibit movement in the other direction. Preferably, a leading edge 65 of each notch is rounded to minimize trauma to the vessel 12.

The notches are positioned at predetermined positions on the first edge 28. As a result, as the first end 36 of the band 22 moves over the outer surface 34 to expand the band 22, the first tab 52 sequentially engages each of the notches. The engagement between the first tab 52 and each of the notches allows each band 22 to expand by sequentially engaging each successive notches but inhibits subsequent contraction towards the contracted configuration 48.

Referring to FIG. 2, when the first tab 52 engages the notch closest to the first end 36, the band 22 in the fully expanded configuration 44. Similarly, referring to FIG. 1 when the first tab 52 engages one of the remaining notches, the band 22 is in one of intermediate expanded configurations 50. Preferably, the notches are positioned proximate the first end 36 so that contraction towards the contracted configuration 48 is only inhibited when each band 22 nears the fully expanded configuration 44 of FIG. 2.

As shown in the Figures, the notches on a distal band 57 and a proximal band 59 of the stent 10 are directed towards each other to minimize trauma to the patient during insertion into the vessel 12.

The protruding lip 58 extends a distance which is also substantially equal to "X" from the second edge 30 of each band 22 proximate the first end 36. The protruding lip 58 extends opposite the receivers 56 and cooperates with the second tab 54 to draw the first tab 52 into each receiver 56 so that the first tab 52 is securely retained in each receiver 56. In the embodiment shown in the Figures, the notches have a depth which is substantially equal to about 0.002 to 0.010 inches. Thus, for the embodiments shown in the Figures, the protruding lip can extend from the second edge a distance of between about 0.002 to 0.010 inches.

Alternately, for example, each receiver 56 could be a triangular tooth (not shown) which extends outwardly from the first edge 28 and the protruding lip 58 could be replaced with an indentation (not shown) into the second edge 30.

Referring to FIG. 4, preferably, each band 22 also includes a retainer 66 for holding each band 22 in substantially the contracted configuration 48 until sufficient force is applied to the inner surface 32 of the band 22 to release the retainer 66 and allow expansion of the band 22. In the embodiments shown in the Figures, the retainer 66 is an adhesive which is disposed in an aperture 68 proximate the first end 36. The adhesive bonds the first end 36 to the outer surface 34 to hold the band 22 in the contracted configuration 48. Preferably, an adhesive, such as NUVA-SIL 5088, which is sold by Loctite Corporation located in Newington, Conn., having a low shear strength and high tensile strength is used so that the adhesive bond readily disengages upon inflation of a balloon 70. With this adhesive, a force of approximately 10 to 100 P.S.I. is required to disengage the adhesive.

Returning to FIG. 2, it may be seen that each band 22 is distributed along a substantially common central axis 62 to form the stent 10. The first end 36 of each band 22 is interconnected by the first elongated strip 24. The positioning of the first elongated strip 24 proximate the first end 36 of each band 22 allows the first elongated strip 24 to also function as a stop which prevents each band 22 from expanding farther than the fully expanded configuration 44. Similarly, each second end 38 of each band 22 is interconnected by the second elongated strip 26.

Importantly, when the stent 10 is configured into the fully expanded configuration 44 shown in FIG. 2 or the contracted configuration 48 shown in FIG. 4, the first elongated strip 24 is positioned relatively close to second elongated strip 26. As a result, the stent 10 is free to flex along an axis defined by the first elongated strip 24 and the second elongated strip 26. This allows the stent 10 to be inserted through curved or winding vessels 11 and allows the stent 10 to be expanded to support curved or winding vessels 11.

Referring to FIG. 1, an outer surface 71 of one of the elongated strips 24, 26 and more preferably the first elongated strip 24 includes a marker 69 which is clearly and easily visible with an x-ray (not shown) to indicate the location of the stent 10 in the vessel. For example, the marker 69 can be a flat gold wire which is spot welded to the stent 10. The gold wire is clearly visible from an x-ray while the remaining portions of the stent 10 appear only faintly on the x-ray. Preferably, a marker 69 is located proximate the distal band 57 and a marker 69 is located proximate the proximal band 59 so that the location of the stent 10 can be precisely determined.

The stent 10 may be fabricated within a range of diameters and overall lengths. Specifically, stents 10 which range in diameter from about 1.0 to 6.0 millimeters and range in length from about ten to forty millimeters have been found to be preferable. The diameter of a given stent 10 is determined, by the length between the first end 36 and the second end 38 of each band 22. The overall length, however, depends on the number of bands 22, the width between the first edge 28 and the second edge 30 of each band 22, and the spacing between the bands 22. Specifically, stents 10 having a width between first edge 28 and the second edge 30 of each band 22 of between about 0.025 millimeters to 1.25 millimeters and spacing between bands 22 of between about 0.025 millimeters to 2.5 millimeters are acceptable.

The embodiment shown in the Figures includes a sequence of ten bands 22. Alternatively, for example, the stent 10 can include a sequence of twenty bands (not shown). It will be appreciated that longer or shorter embodiments with additional or less bands 22 are envisioned by the present invention. Structurally, longer sequences of bands 22 may require additional support. Therefore, in cases where longer sequences of bands 22 are needed, it may be desirable to increase the width between the first edge 30 and the second edge 32 of one or more bands 22 and/or provide additional interconnections between one or more of the bands 22.

MANUFACTURING

One method for fabricating a stent 10 according to the present invention begins by photo-chemical milling of a flat sheet of full hard, implant grade, 316L stainless steel. The photo-chemical milling is used to produce the bands 22, the first elongated strip 24, the second elongated strip 26, the tabs 52, 54, the receivers 56 and the protruding lip 58 in an unrolled configuration shown in FIG. 6. Next, the tabs 52, 54 are annealed to provide flexibility to the tabs 52, 54. After annealing of the tabs 52, 54, the flat sheet is finished using electropolishing or some other surface treatment known by those skilled in the art and the markers 69 are manufactured into the first elongated strip 24.

Subsequently, the flat sheet can be rolled around a mandrel (not shown) to form the stent 10 having an equilibrium configuration 46 which is substantially equal to the diameter of the mandrel. Preferably, the flat sheet is rolled so that movement of each band 22 between the contracted configuration 48 and the fully expanded configuration 44 is within the elastic limits of each band 22. Further, each band 22 is rolled so that the equilibrium configuration 46 is between the contracted configuration 48 and the fully expanded configuration 44.

For example, the flat sheet could be rolled around a mandrel having a diameter (not shown) which is approximately equal to 1.45 millimeters. Thus, the stent 10 would have a diameter 42 at the equilibrium configuration 46 of approximately 1.45 millimeters. In this embodiment, each band 22 of the stent 10 is designed to have a diameter 42 at the contracted configuration 48 of approximately 1.25 millimeters, a diameter 42 at the intermediate expanded configurations 50 within the range of between about 1.8 millimeters to about 2.5 millimeters and a diameter 42 at the fully expanded configuration 44 of about 2.6 millimeters. Also, for this embodiment, each band 22 has a diameter 42 of approximately 0.040 millimeters at the compressed elastic limit and a diameter 42 of approximately 3.1 millimeters at the expanded elastic limit.

Depending upon the requirements of the operation, the diameter 42 of the equilibrium configuration 46 can be designed to be only slightly greater than the diameter 42 at the contracted configuration 48 or can be designed to be only slightly less than the diameter 42 at the intermediate expanded configurations 50. A stronger retainer 66, e.g., a stronger adhesive, is required if the expanded configuration 46 is proximate the intermediate expanded configurations 50.

Next, the first tab 52 and the second tab 54 are bent over the outer surface 34 to secure the tabs 52, 54 to their respective bands 22. The tabs 52, 54 were previously annealed so that they do not break from the band 22 during this procedure. Since the tabs 52, 54 are bent after the bands 22 are rolled, the stent 10 is relatively easy to manufacture.

Subsequently, after rolling, the stent 10 can be passivated, i.e., applying an oxide surface coating which is corrosion resistant and is relatively inert. Additionally, other coatings may be applied to the stent 10, such as anti-coagulent coatings, neointimal proliferation inhibitors, or radioactive coatings.

Now the stent 10 is ready for placement into the vessel 12.

OPERATION

Insertion of the stent 10 into the vessel 12 (or other part of the body) begins, by placement of the stent 10 in the equilibrium configuration 46 over a deflated, inflatable balloon catheter 70. Next, the bands 22 are compressed. This causes each of the bands 22 to move substantially iso-concentrically to adopt substantially the contracted configuration 48. When the bands 22 have adopted the contracted configuration 48, the retainer 66 is used to secure some or all of the bands 22 in the contracted configuration 48. The retainer 66, e.g., an adhesive disposed in tab aperture 68 holds the bands 22 in position over the inflatable balloon 70 in a manner as best seen in FIG. 4.

Once the stent 10 has been configured in the contracted configuration 48 of FIG. 4, and locked around the inflatable balloon 70, a placement catheter 72 is inserted into the vessel 11 where the stent 10 is to be deployed. The stent 10 and balloon 70 are then advanced through the placement catheter 72 and into the vessel 11 and towards a target site. The markers 69 on the stent 10 allows the doctor to precisely position the stent 10 at the target site.

Once the balloon 70 and the stent 10 are placed substantially adjacent the target site, the balloon 70 is partially inflated. The partial inflation of the balloon 70 breaks the adhesive bond and releases the bands 22 from the balloon.

Once the bands 22 are released, the resilient material of the bands 22 causes the bands 22 to move from the contracted configuration 48 of FIG. 4 towards equilibrium configuration 46 of FIG. 3. Since the contracted configuration 48 is within the elastic limits of the band 22, each band 22 will not plastically deform and will return proximate to the equilibrium configuration 46 absent any external force from the vessel 12.

Subsequently, the balloon 70 may then be more fully inflated to expand each of the bands 22 as required. As each band 22 expands, the first tab 32 sequentially engages the receivers 56. During this action, the second tab 54 interacts with the protruding lip 58 to securely draw the first tab 52 into the receiver 56. Also, the relief 64 allows the first and second tabs 52, 54 to separate as the first tab 56 moves over the receivers 56 and pull together when the first tab 32 engages a specific receiver 56.

In particular, each band 22 may be expanded until the first tab 52 engages one of the receivers 56. Depending upon which receiver 56 is engaged by the first tab 52, each band 22 can be positioned in one of the intermediate expanded configurations 50 as shown in FIG. 1 or the fully expanded configuration 44 of FIG. 2. Importantly, each band 22 may be individually expanded to reach an individual degree of expansion to suit the specific need of the patient. In this fashion, the stent 10 may be adapted to support tapered or otherwise irregular vessels 12. Once the stent 10 has been properly expanded, the balloon 70 may be deflated and the balloon 70 and placement catheter 72 may be removed, completing the procedure.

Since each band 22 is expanded within its elastic limits, each band 22 wants to return its equilibrium configuration 46. This causes the first tab 52 to securely engage the specific receiver 56 and securely retain the stent 10 in position.

In some cases, internal pressure within a vessel 12 may exceed the strength of a particular vascular segment. In such cases, the present invention may be reconfigured to add a thin layer of substrate or material (not shown), such as Rayon, over the bands 22 to form a reinforcing stent (not shown). Insertion of the modified reinforcing stent generally follows the operational sequence outlined in the preceding paragraphs.

While the particular expandable stent 10 as herein shown and disclosed in detail is fully capable of obtaining the objects and providing the advantages herein before stated, it is to be understood that this is merely illustrative of the presently preferred embodiments of the invention. For example, in some embodiments, the balloon 70 may be replaced with some other device (not shown), such as a small actuator, which can move the stent 10 from the contracted configuration 40 to one of the intermediate expanded configurations 50 or the fully expanded configuration 44 in the vessel 12. Therefore, no limitations are intended to the details of construction or design herein shown other than as described in the appended claims.

What is claimed is:

1. A stent for placement in a vessel, the stent comprising a plurality of interconnected, tubular shaped bands, at least one of the bands comprising:

a first end overlapping a second end and being moveable relative to the second end to reconfigure the band between at least a contracted configuration and a fully expanded configuration;

at least one receiver disposed on a first edge proximate one of the ends; and a first tab projecting from the first edge proximate the other one of the ends, the first tab including a receiver section that extends substantially radially from the first edge, the receiver section being shaped to engage the receiver and inhibit the band from retracting towards the contracted configuration.

2. The stent of claim 1 comprising a retainer which retains at least one of the bands substantially in the contracted configuration and releases the band when pressure is applied to the band.

3. The stent of claim 1 wherein the band includes a plurality of spaced apart receivers formed in the first edge, proximate the first end and each receiver comprises a notch having a notch depth and wherein the first tab cantilevers from the first edge proximate the second end and extends upwardly and around an outer surface of the band.

4. The stent of claim 3 wherein the band includes an outwardly protruding lip extending a lip distance which is substantially equal to the notch depth from a second edge, substantially opposite the receivers and a second tab projecting from the second edge, proximate the second end, the second tab extending upwardly and around the outer surface of the band and interacting with the protruding lip to draw the first tab into engagement with the notches.

5. The stent of claim 4 wherein the band includes a relief proximate the first tab and the second tab which allows the first tab and the second tab to separate to facilitate movement of the first tab over the receivers.

6. The stent of claim 4 wherein at least a portion of at least one of the tabs is annealed.

7. The stent of claim 4 wherein the band includes a stop which inhibits the band from expanding farther than the fully expanded configuration.

8. The stent of claim 1 comprising at least one marker which allows for clear and easy indicating of the location of the stent in the vessel.

9. A stent for placement in a vessel, the stent comprising a plurality of interconnected, tubular shaped bands, at least one of the bands comprising:
    a first end overlapping a second end and being moveable relative to the second end to reconfigure the band between at least a contracted configuration and a fully expanded configuration; and
    a retainer which retains the band substantially in the contracted configuration and releases the band when sufficient pressure is applied to the band.

10. The stent of claim 9 wherein the retainer includes an adhesive for selectively securing the first end to an outer surface of the band.

11. The stent of claim 9 wherein the band includes at least one receiver disposed on a first edge proximate one of the ends, and a first tab projecting from the first edge proximate the other one of the ends, the first tab including a receiver section that is on a plane that is substantially perpendicular to a central axis of the band, the receiver section being shaped to engage the receiver and inhibit the band from retracting towards the contracted configuration.

12. The stent of claim 11 wherein each receiver comprises a notch having a notch depth, the band includes an outwardly protruding lip extending a distance which is substantially equal to the notch depth from a second edge, substantially opposite the receiver, and the band includes a second tab projecting from the second edge, proximate the second end, the second tab extending upwardly and around the outer surface of the band and interacting with the protruding lip to draw the first tab into engagement with the notch.

13. A stent for placement in a vessel, the stent comprising a plurality of interconnected, tubular shaped bands, each of the bands comprising:
    a first end overlapping a second end and being moveable relative to the second end to reconfigure each band between a contracted configuration and a fully, expanded configuration;
    a plurality of spaced apart receivers formed in a first edge proximate the first end, wherein, each receiver comprises a notch having a notch depth;
    an outwardly protruding lip extending a lip distance which is substantially equal to the notch depth from a second edge substantially opposite the receivers;
    a first tab which cantilevers from the first edge proximate the second end, the first tab extending upwardly and around an outer surface of the band, the first tab being suited to engage the notches and inhibit the tubular band from retracting towards the contracted configuration; and
    a second tab which cantilevers from the second edge proximate the second end, the second tab extending upwardly and around the outer surface of the band for interacting with the protruding lip to draw the first tab into engagement with the notches.

14. The stent of claim 13 comprising a relief proximate the first end between the first tab and the second tab which allows the first tab and the second tab to separate to facilitate movement of the first tab over the receivers.

15. A stent for placement in a vessel, the stent comprising a plurality interconnected, tubular shaped bands, at least one of the bands comprising a first end overlapping a second end and being moveable relative to the second end to reconfigure the band between a contracted configuration and a fully expanded configuration, the band being made from a resilient material that is formed so that movement between the contracted configuration and the expanded configuration is within the elastic limits of the band and is formed so that an equilibrium configuration of the band is between the contracted configuration and the fully expanded configuration.

16. The stent of claim 15 wherein the band includes at least one receiver disposed on a first edge proximate one of the ends, and a first tab which cantilevers from the first edge proximate the other one of the ends, the first tab including a receiver section that extends substantially radially outwardly from the first edge, the receiver section being shaped to engage the receiver and inhibit the band from retracting towards the contracted configuration.

17. The stent of claim 16 wherein each receiver comprises a notch having a notch depth, the band includes an outwardly protruding lip extending a distance which is substantially equal to the notch depth from a second edge, substantially opposite the receiver, and the band includes a second tab projecting from the second edge, proximate the second end, the second tab extending upwardly and around the outer surface of the band and interacting with the protruding lip to draw the first tab into engagement with the notch.

18. A stent prepared by a process comprising the steps of:
    forming a plurality interconnected, tubular shaped bands in a substantially flat sheet of resilient material, each band having a first end and an opposed second end; and
    rolling the sheet so that the first end of each band overlaps its second end, is moveable relative to its second end within elastic limits of the band to reconfigure the band between a contracted configuration and a fully expanded configuration and has an equilibrium configuration that is between the contracted configuration and the fully expanded configuration.

19. The process of claim 18 wherein each band is formed to include a first tab extending from a first edge of the band proximate the second end and a second tab extending from a second edge of the band proximate the second end and the process includes the step of bending the first and second tabs over the an outer surface of the band after the flat sheet has been rolled.

20. A method for placing a stent at a target site in a vessel, the method comprising the steps of:
    securing a stent in a substantially contracted position, with a retainer, to a balloon, the stent comprising a plurality of interconnected, tubular shaped, bands, at least one of the bands comprising a first end overlapping a second end and being moveable relative to the second end to reconfigure the band between the contracted configuration and a fully expanded configuration;
    advancing the balloon and stent in the vessel until the balloon and stent are positioned substantially adjacent the target site;

releasing the retainer by partly inflating the balloon; and allowing the bands to expand from the contracted configuration.

21. The method of claim 20 comprising the step of securing at least one of the bands proximate the fully expanded configuration with a first tab which cantilevers from a first edge of the band, the first tab having a receiver section that extends substantially radially from the first edge and that interacts with at least one receiver, the receiver being disposed proximate one of the ends and the first tab being disposed proximate the other one of the ends.

22. A method for placing a stent at a target site in a vessel, the method comprising the steps of:

securing a stent to a balloon, the stent comprising a plurality of interconnected, tubular shaped, bands, at least one of the bands comprising a first end overlapping a second end and being moveable relative to the second end to reconfigure the band between a contracted configuration and a fully expanded configuration;

advancing the balloon and stent in the vessel until the balloon and stent are positioned substantially adjacent the target site;

expanding the bands with the balloon; and securing at least one of the bands proximate the fully expanded configuration with a first tab which cantilevers from a first edge of the band, the first tab having a receiver section that extends substantially radially from the first edge of the band and that interacts with at least one receiver, the receiver being disposed proximate one of the ends of the band and the first tab being disposed proximate the other one of the ends of the band.

23. The method of claim 22 wherein the step of securing the stent includes using a retainer that is released upon inflation of the balloon to secure the stent.

* * * * *